United States Patent [19]

Rönnberg et al.

[11] Patent Number: 5,788,685
[45] Date of Patent: Aug. 4, 1998

[54] DISPOSABLE DIAPER HAVING ELASTICIZED LEG CUFFS

[75] Inventors: Peter Rönnberg, Mölndal; Robert Kling, Skene, both of Sweden

[73] Assignee: Mölnlycke AB, Göteborg, Sweden

[21] Appl. No.: 637,690

[22] PCT Filed: Nov. 14, 1994

[86] PCT No.: PCT/SE94/01066

§ 371 Date: Jun. 12, 1996

§ 102(e) Date: Jun. 12, 1996

[87] PCT Pub. No.: WO95/13772

PCT Pub. Date: May 26, 1995

[30] Foreign Application Priority Data

Nov. 15, 1993 [SE] Sweden .................................. 9303748

[51] Int. Cl.⁶ .................................................. A61F 13/15
[52] U.S. Cl. .................................................. 604/385.2
[58] Field of Search .................... 604/373, 385.1, 604/385.2, 386, 387, 301, 393, 396–398

[56] References Cited

U.S. PATENT DOCUMENTS

| | | |
|---|---|---|
| 4,050,462 | 9/1977 | Woon et al. . |
| 4,437,860 | 3/1984 | Sigl et al. . |
| 4,486,192 | 12/1984 | Sigl . |
| 4,762,582 | 8/1988 | de Jonckheere . |
| 4,854,989 | 8/1989 | Singheimer . |
| 4,900,317 | 2/1990 | Buell . |
| 4,936,840 | 6/1990 | Proxmire ................................. 604/391 |
| 4,938,754 | 7/1990 | Mesek ................................. 604/385.2 |
| 5,176,671 | 1/1993 | Roessler et al. ........................ 604/386 |
| 5,187,817 | 2/1993 | Zolner ................................. 604/393 |

FOREIGN PATENT DOCUMENTS

| | | |
|---|---|---|
| 0 027 303A1 | 4/1981 | European Pat. Off. . |
| 532034A2 | 3/1993 | European Pat. Off. ............... 604/392 |
| 2586558 | 3/1987 | France ................................. 604/391 |
| 446 939 | 10/1986 | Sweden . |
| 1520740 | 8/1978 | United Kingdom .................... 604/391 |
| 2 063 677 | 6/1981 | United Kingdom . |
| 2 108 368 | 5/1983 | United Kingdom . |
| 2 112 270 | 7/1983 | United Kingdom . |
| 2 146 887 | 5/1985 | United Kingdom . |
| 2 173 689 | 10/1986 | United Kingdom . |
| 2 263 622 | 8/1993 | United Kingdom . |
| 2 275 610 | 9/1994 | United Kingdom . |

*Primary Examiner*—Robert A. Clarke
*Attorney, Agent, or Firm*—Burns, Doane, Swecker & Mathis, L.L.P.

[57] ABSTRACT

A disposable diaper (10) is disclosed in which the elastic (24) which provides elasticized leg cuffs extends along substantially the entire length of each of the longitudinal edge portions (25) of the diaper between fastening means (30,32) on front and rear waist portions (20, 22 resp.) for fastening the diaper around a wearer.

12 Claims, 2 Drawing Sheets

DISPOSABLE DIAPER HAVING ELASTICIZED LEG CUFFS

BACKGROUND OF THE INVENTION

This application is a 371 application of PCT/SE94/01066, filed Nov. 14, 1994.

The present invention relates to a disposable diaper according to the preamble of claim 1.

DISCUSSION OF RELATED ART

For reasons of comfort and fit, it is nowadays common to provide diapers in different sizes. For example, infants' diapers are available in a certain range of sizes including newborn, toddler, etc. For adults suffering from incontinence, due to the large disparity in the size of adults as well as the various absorption requirements placed on the diapers, a wide range of different sized diapers is required. In terms of cost-effectiveness, it is optimal to have a single size which conforms to most adults.

In order to reduce the risk of leakage, it is known to provide diapers with elasticized leg cuffs. Typical of such diapers are those disclosed in U.S. Pat. No. 4 437 860, U.S. Pat. No. 4 486 192, GB-B-2 143 115, U.S. Pat. No. 4050462, SE-B-446939 and GB-A-2063677. In these known diapers, the elastic ribbon in the elasticized leg cuffs extends along each longitudinal edge portion of the diaper in the vicinity of the crotch portion of the diaper. At either end of the crotch portion, wider waist portions are provided within which the elastic ribbon terminates at a distance from the longitudinal edge portion of the diaper. Fastening means such as hook-and-loop fasteners are provided at the longitudinal edge portions of the waist portions for fastening the diaper around the wearer.

SUMMARY

It is an object of the present invention to provide a disposable diaper which may be comfortably worn by persons of differing size.

This object is achieved in accordance with the present invention by a disposable diaper according to claim 1.

Preferred embodiments of the present invention are detailed in the dependent claims.

BRIEF DESCRIPTION OF THE DRAWINGS:

The invention will be described in greater detail in the following by way of example only and with reference to the attached drawings, in which.

Figure 1:
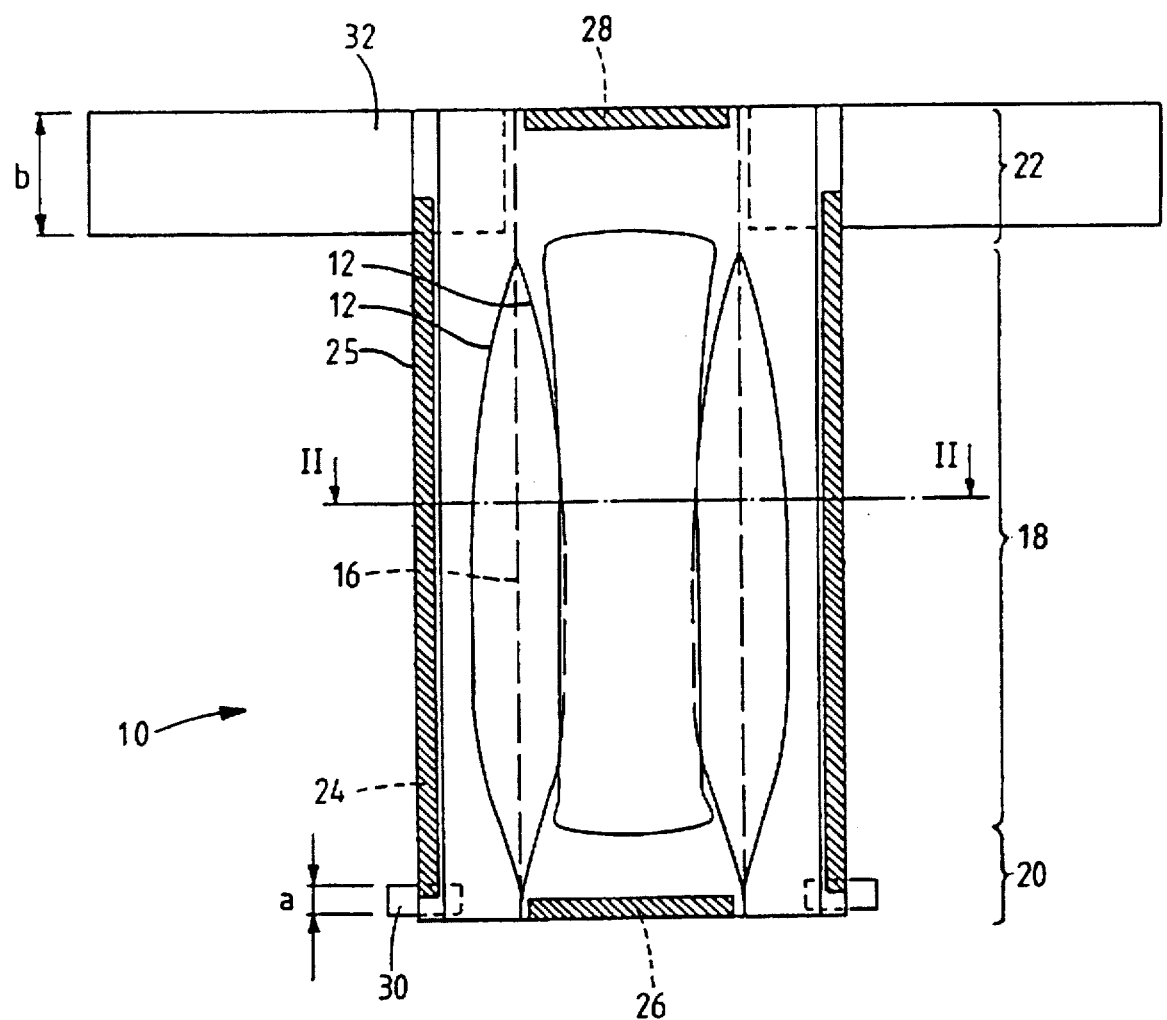
FIG. 1 is a plan view of an absorbent article in accordance with the present invention having elasticized leg cuffs, the article being illustrated during a stage of the manufacturing process.

DETAILED DESCRIPTION OF PREFERRED EMBODIMENTS:

In the drawing, an absorbent article in the form of a disposable diaper is generally denoted by reference numeral 10. For reasons of clarity, the diaper 10 is shown in FIG. 1 in a stage occupied by the diaper during its manufacture. Accordingly, reference numeral 12 denotes joining lines, for example glue lines or heat bonding lines, about which the diaper is gathered in a manner known per se to form a pair of inner cuffs 14 (FIG. 2) through which an elastic chord 16 runs. Due to the gathering of the diaper about the joining lines 12, the diaper adopts a generally hour glass shape with a narrow centrally disposed crotch portion 18 and wider front and rear waist portions 20, 22 respectively at transverse end regions of the crotch portion.

The diaper 10 is provided with prestretched elastic means 24 disposed along longitudinal edge portions 25 of the diaper. Advantageously, the waist portions 20, 22 may be provided with transversely extending elastic means 26, 28 respectively.

To permit the diaper to be fastened around a wearer, fastening means are provided at the waist portions. As illustrated in FIG. 1, the front waist portion 20 which would normally be disposed at the front of the wearer may be provided with a pair of fastening means such as hook members 30, with each hook member 30 extending substantially perpendicularly from the longitudinal edge portion 25 of the diaper. The fastening means may further comprise a belt 32 extending substantially perpendicularly from the rear waist portion 22 which portion, during use, is normally disposed at the back of the wearer. As illustrated in FIG. 1, the belt may be in two halves, with each half extending from the opposed longitudinal edge portions 25 of the diaper. The two belt halves are intended to pass around the waist of the wearer and are fastened together at the front of the wearer by any suitable means such as a hook and loop fastener. Preferably, the belt is made from a nonwoven material which acts as a loop fastener for the hook members 30.

Figure 2:
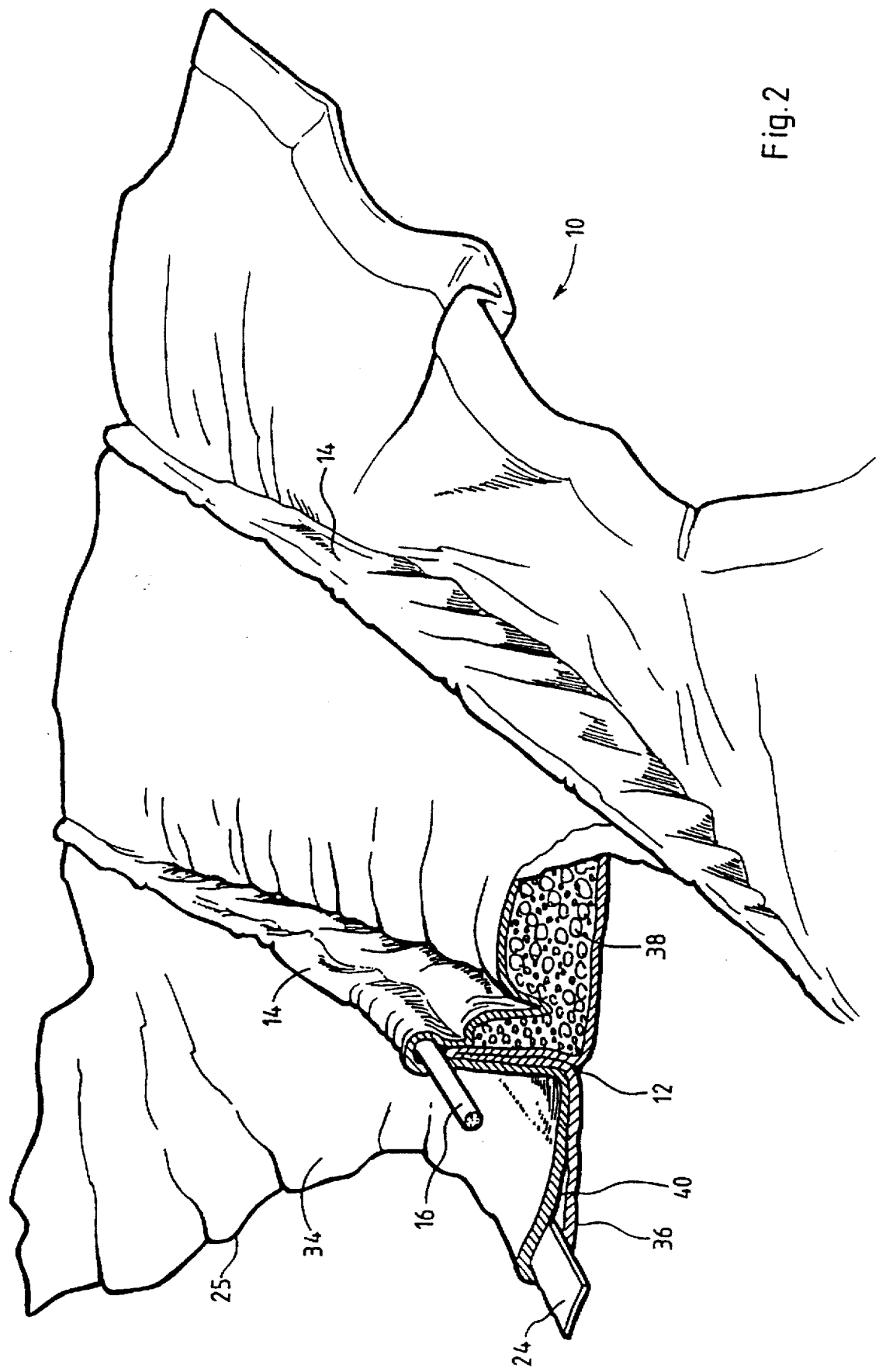
FIG. 2 is a partial sectional perspective view taken substantially along the line II—II of FIG. 1, though with the article in a finished condition.

The structure of the diaper of FIG. 1 will be more easily understood from the partial sectional view through the crotch portion 18, as illustrated in FIG. 2. In keeping with the present invention, the diaper 10 has a generally hour glass shape and includes a facing sheet 34, a backing sheet 36 and an absorbent core 38 sandwiched between the facing and backing sheets 34, 36 respectively. The specific components used to form the illustrated diaper may be any of the types commonly used for such purposes. For example, the facing sheet 34 may be any soft flexible liquid permeable material such as a nonwoven fibrous web having a basis weight of around 20 g/m². The backing sheet 36 is made from a liquid impermeable material such as a thin (for example 20μ) plastic film of polyethylene, polypropylene, polyvinylchloride or the like. The absorbent core 38 may comprise wood pulp fibres, air-laid tissue, various superabsorbent materials, etc.

As mentioned above with reference to FIG. 1, prestretched elastic means 24 are disposed along the longitudinal edge portions 25 of the diaper. As clearly shown in FIG. 2, the elastic means 24 may be in the form of an elongate elastic ribbon. The elastic ribbon is preferably relatively wide, for example between 1 and 2 cm, preferably about 1.5 cm, so as to reduce the tendency for the leg cuff to mark the wearer. The elastic ribbon may be incorporated in the diaper in any known manner, though preferably in the manner disclosed in our copending Swedish patent application with the title "Disposable diaper having elasticized leg cuffs".

In accordance with the present invention, the elastic means 24 extend along substantially the entire length of the longitudinal edge portions 25 between the fastening means on the front and rear waist portions 20, 22 respectively. This implies that when the diaper is being fastened to the wearer, a tensioning force exerted during the fastening operation on the fastening means 30 on the front waist portion 20 will directly cause the elastic means 24 to expand, thereby ensuring a tighter fit of the leg cuffs about the wearer.

To further enhance the comfort of the wearer of the diaper, it is advantageous if the fastening means 32 on the rear waist portion 22 present a relatively large engagement surface for receiving the fastening means on the front waist portion 20. Thus, the fastening means 30 on the front waist portion 20 preferably project substantially perpendicularly from the longitudinal edge portions 25 of the diaper, with the fastening means having a predetermined width a. Similarly, the fastening means 32 on the rear waist portion 22 project substantially perpendicularly from the longitudinal edge portions 25 of the diaper, with these fastening means having a predetermined width b. The percentage ratio of the width a of the fastening means 30 on the front waist portion 20 to the width b of the fastening means 32 on the rear waist portion 22 preferably lies between about 10% and about 30%, most preferably about 25%.

When the fastening means 30 on the front waist portion 20 comprise a pair of opposed hook members, their width a may be between about 15 mm and about 45 mm, preferably about 30 mm.

When the fastening means 32 on the rear waist portion 22 are a pair of opposed loop fasteners, the width b may be between about 50 mm and about 150 mm, preferably about 120 mm. Advantageously, the opposed loop fasteners are in the form of a nonwoven belt, though they may comprise regions of hook-engaging material affixed to or incorporated in the rear waist portion 22.

Thus, when the diaper is being fastened around a wearer, tension is applied to the fastening means 30 on the front waist portion 20 until the leg elastic 24 is sufficiently stretched. The fastening means 30 can then be affixed to the fastening means 32 on the rear waist portion. The tension can be readily adjusted by moving the fastening means 30 over the width of the fastening means 32 on the rear waist portion.

The present invention is not restricted to the embodiments described above and illustrated by way of example in the drawings, but may be varied within the scope of the appended claims. It is to be understood that the term "diaper" is intended to encompass absorbent articles of the type disclosed in the appended claims which are worn by infants and adults alike. The terms "front" waist portion and "rear" waist portion denote the positioning of these portions during normal intended use of the diaper, though it is conceivable that these portions be reversed, e.g. that hook members be provided on the "rear" waist portion and loop fasteners on the "front" waist portion. It will be apparent to the skilled person that suitable fastening means other than hook and loop fasteners, e.g. releasable adhesives, may be employed

We claim:

1. A disposable diaper comprising:

a facing sheet;

a backing sheet;

an absorbent core disposed between the facing sheet and the backing sheet;

said diaper having an hour glass shape with a centrally disposed crotch portion, a front waist portion at one transverse end region of said crotch portion and a rear waist portion at another transverse end region of said crotch portion, said waist portions being wider than said crotch portion;

said front waist portion being provided with first fastening means having a first predetermined width and said rear waist portion being provided with second fastening means having a second predetermined width, said first and second fastening means being adapted for fastening the diaper around a wearer;

prestretched elastic means disposed along longitudinal edge portions of said diaper for providing predetermined gathered and substantially non-gathered regions along said edge portions;

said elastic means extending along substantially an entire length of said longitudinal edge portions from said first fastening means on said front waist portion to said second fastening means on said rear waist portion;

said second fastening means including a belt extending substantially perpendicularly from the rear waist portion, said belt being adapted to pass around a waist of the wearer;

said first predetermined width being between about 10% and 30% of said second predetermined width.

2. The disposable diaper according to claim 1, wherein said elastic means is an elastic ribbon.

3. The disposable diaper according to claim 1, wherein said first fastening means on said front waist portion project substantially perpendicularly from said longitudinal edge portions of said diaper.

4. The disposable diaper according to claim 1, wherein said second fastening means on said rear waist portion project substantially perpendicularly from said longitudinal edge portions of said diaper.

5. The disposable diaper according to claim 1, wherein said first fastening means on said front waist portion are a pair of opposed hook members, the predetermined width of which lies between about 15 mm and about 45 mm.

6. The disposable diaper according to claim 5, wherein the predetermined width of said first fastening means on said front waist portion is about 30 mm.

7. The disposable diaper according to claim 1, wherein said second fastening means on said rear waist portion are a pair of opposed loop fasteners, predetermined the width of which lies between about 50 mm and about 150 mm.

8. The disposable diaper according to claim 7, wherein said opposed loop fasteners are in the form of a nonwoven belt.

9. The disposable diaper according to claim 7, wherein the predetermined width of said second fastening means on said rear waist portion is about 120 mm.

10. The disposable diaper according to claim 1, wherein the percentage ratio is about 25%.

11. The disposable diaper according to claim 1, wherein the longitudinal edge portions constitute outer-most edges of the diaper.

12. The disposable diaper according to claim 1, wherein said first fastening means is securable to said second fastening means for fastening the diaper around the wearer.

\* \* \* \* \*